US008383347B1

(12) United States Patent
Cao et al.

(10) Patent No.: US 8,383,347 B1
(45) Date of Patent: Feb. 26, 2013

(54) METHOD OF DIAGNOSING OR ASSESSING RISK FOR PARKINSON'S DISEASE OR ALZHEIMER'S DISEASE USING TCR CLONALITY

(75) Inventors: Chuanhai Cao, Temple Terrace, FL (US); Xiaoyang Lin, Tampa, FL (US); Huntington Potter, Tampa, FL (US)

(73) Assignee: University of South Florida, Tampa, FL (US)

(*) Notice: Subject to any disclaimer, the term of this patent is extended or adjusted under 35 U.S.C. 154(b) by 341 days.

(21) Appl. No.: 12/772,728

(22) Filed: May 3, 2010

Related U.S. Application Data

(60) Provisional application No. 61/174,833, filed on May 1, 2009.

(51) Int. Cl.
  *C12Q 1/68* (2006.01)
  *C12P 19/34* (2006.01)
(52) U.S. Cl. .................................. 435/6.12; 435/91.2
(58) Field of Classification Search ............... 435/6.12, 435/91.2
  See application file for complete search history.

(56) References Cited

U.S. PATENT DOCUMENTS

| 4,219,411 | A | 8/1980 | Yen et al. | |
|---|---|---|---|---|
| 4,624,915 | A | 11/1986 | Schindler et al. | |
| 4,672,040 | A | 6/1987 | Josephson | |
| 5,837,200 | A | 11/1998 | Diessel et al. | |
| 5,837,447 | A | 11/1998 | Gorski | |
| 5,914,262 | A | 6/1999 | MacMichael et al. | |
| 2005/0010030 | A1* | 1/2005 | Zang et al. | 530/350 |
| 2007/0117134 | A1* | 5/2007 | Kou | 435/6 |
| 2010/0022440 | A1* | 1/2010 | Monson | 514/2 |
| 2010/0151471 | A1* | 6/2010 | Faham et al. | 435/6 |

OTHER PUBLICATIONS

Antonaci et al., Senile Dementia, Alzheimer Type: A Distinct Entity in the Immunosenescence?, Journal of Clinical Laboratory Analysis, 1990, vol. 4, pp. 16-21.
Bakacs et al., Some Aspects of Complementarity in the Immune System, International Archives of Allergy and Immunology, 2001, vol. 126, pp. 23-31.
Bakacs et al., T Cells Survey the Stability of the Self: A Testable Hypothesis on the Homeostatic Role of TCR-MHC Interactions, International Archives of Allergy and Immunology, 2007, vol. 144, pp. 171-182.
Breitbart et al., Altered Memory B-Cell Homeostasis in Human Aging, Journal of Gerontology: Biological Sciences, 2002, vol. 57A, No. 8, pp. B304-B311.
Cao et al., Successful Adjuvant-Free Vaccination of BALB/c Mice with Mutated Amyloid Beta Peptides, BMC Neuroscience, 2008, vol. 9, No. 25, pp. 1-11.
Colonna-Romano et al., B Cell Immunosenescence in the Elderly and in Centenarians, Rejuvenation Research, 2008, vol. 11, No. 2, pp. 433-439.
Contini et al., Soluble HLA-A,-B,-C and -G Molecules Induce Apoptosis in T and NK CD8+ Cells and Inhibit Cytotoxic T Cell Activity Through CD8 Ligation, Eur. J. Immunol., 2003, vol. 33, pp. 125-134.
Dickey et al., Duration and Specificity of Humoral Immune Responses in Mice Vaccinated with the Alzheimer's Disease-Associated Beta-Amyloid 1-42 Peptide, DNA and Cell Biology, 2001, vol. 20, No. 11, pp. 723-729.
Dillon et al., Molecular Complementarity II: Energetic and Vectorial Basis of Biological Homeostasis and Its Implications for Death, J. Theor. Biol., 1997, vol. 188, pp. 481-493.
Eggleton et al., Fractionation of Human Neutrophils into Subpopulations by Countercurrent Distribution: Surface Charge and Functional Heterogeneity, European Journal of Cell Biology, 1992, vol. 57, pp. 265-272.
Ethell et al., ABeta-Specific T-Cells Reverse Cognitive Decline and Synaptic Loss in Alzheimer's Mice, Neurobiology of Disease, 2006, vol. 23, pp. 351-361.
Ishizaka et al., Soluble T-Cell Products Antigenically Related to T-Cell Receptors, Cytokine, 1995, vol. 7, No. 3, pp. 260-266.
Janeway et al., Cytokines and Cytokine Receptors, Immunology, 2001, Garland Publishing, New York, ed. 5th, pp. 120-129.
Jerne, The Somatic Generation of Immune Recognition, Eur. J. Immunol., 1971, vol. 1, pp. 1-9.
Jinushi et al., Therapy-Induced Antibodies to MHC Class I Chain-Related Protein a Antagonize Immune Suppression and Stimulate Antitumor Cytotoxicity, PNAS, 2006, vol. 103, No. 24, pp. 9190-9195.
Jones et al., The Role of Soluble Receptors in Cytokine Biology: The Agonistic Properties of the sIL-6R/IL-6 Complex, Biochimica et Biophysica Acta 1592, 2002, pp. 251-263.
Gaskin et al., Human Antibodies Reactive with Beta-Amyloid Protein in Alzheimer's Disease, J. Exp. Med., 1993, vol. 177, pp. 1181-1186.
Gaskin et al., Autoantibodies to Neurofibrillary Tangles and Brain Tissue in Alzheimer's Disease, J. Exp. Med., 1987, vol. 165, pp. 246-250.
Matzinger et al., The Danger Model: A Renewed Sense of Self, Science, 2002, vol. 296, pp. 301-305.
Monsonego et al., Immunotherapeutic Approaches to Alzheimer's Disease, Science, 2003, vol. 302, pp. 834-838.

(Continued)

*Primary Examiner* — Kenneth R. Horlick
(74) *Attorney, Agent, or Firm* — Robert J. Varkonyi; Smith & Hopen, P.A.

(57) ABSTRACT

Changes in adaptive immune system were identified and correlated as a predictor of $A\beta_{40}$ and $A\beta_{42}$ and AD progression. T-cell, B-cell, TCR and BCR profiles were used to correlate clinical progression of AD. The CDR3 region was spectratyped, showing the clonality of the CDR3 region. This intrafamily gene fragment length profile was compared to age-matched controls, thereby indicating the existence of a neurodegenerative disease. The novel method is useful in diagnosing neurodegenerative disease, like Parkinson's disease, HIV-associated Dementia, or Alzheimer's disease. Moreover, this permits the clinical identification of patients at a very early stage of AD and/or monitoring the potential benefits of disease modifying therapeutics.

20 Claims, 8 Drawing Sheets

OTHER PUBLICATIONS

Morgan et al., ABeta Peptide Vaccination Prevents Memory Loss in an Animal Model of Alzheimer's Disease, Nature, 2000, vol. 408, pp. 982-985.

Motz et al., Persistence of Lung CD8 T Cell Oligoclonal Expansions upon Smoking Cessation in a Mouse Model of Cigarette Smoke-Induced Emphysema, The Journal of Immunology, 2008, vol. 181, pp. 8036-8043.

Nishio et al., Development of TCRB CDR3 Length Repertoire of Human T Lymphocytes, International Immunology, 2004, vol. 16, No. 3, pp. 423-431.

Otsuka et al., Rapid Appearance of Beta-Amyloid Precursor Protein Immunoreactivity in Damaged Axons and Reactive Glial Cells in Rat Brain Following Needle Stab Injury, Brain Research, 1991, vol. 568, pp. 335-338.

Puellmann et al., A Variable Immunoreceptor in a Subpopulation of Human Neutrophils, PNAS, 2006, vol. 103, No. 39, pp. 14441-14446.

Richartz-Salzburger et al., Altered Lymphocyte Distribution in Alzheimer's Disease, Journal of Psychiatric Research, 2007, vol. 41, pp. 174-178.

Rogers et al., Expression of Immune System-Associated Antigens by Cells of the Human Central Nervous System: Relationship to the Pathology of Alzheimer's Disease, Neurobiology of Aging, 1988, vol. 9, pp. 339-349.

Singh, Immune-Activation Model in Alzheimer Disease, Molecular and Chemical Neuropathology, 1996, vol. 28, pp. 105-111.

Slifka et al., Functional Avidity Maturation of CD8+T Cells Without Selection of Higher Affinity TCR, Nature Immunology, 2001, vol. 2, No. 8, pp. 711-717.

Solomon, Psychoneuroimmunology: Interactions Between Central Nervous System and Immune System, Journal of Neuroscience Research, 1987, vol. 18, pp. 1-9.

Thimme et al., Determinants of Viral Clearance and Persistence During Acute Hepatitis C Virus Infection, J. Exp. Med., 2001, vol. 194, No. 10, pp. 1395-1406.

Weksler et al., The Effect of Age on the B-Cell Repertoire, Journal of Clinical Immunology, 2000, vol. 20, No. 4, pp. 240-249.

Wilcock et al., Microglial Activation Facilities ABeta Plaque Removal Following Intracranial Anti-ABeta Antibody Administration, Neurobiology of Disease, 2004, vol. 15, pp. 11-20.

Yoo et al., Innate and Acquired Immunity Intersect in a Global View of the Acute-Phase Response, PNAS, 2003, vol. 100, No. 3, pp. 1157-1162.

Nishio et al. 2004. "Development of TCRB CDR3 Length Repertoire of Human T Lymphocytes." International Immunology. vol. 16. No. 3. pp. 423-431.

* cited by examiner

| Clones | Seq ID No. | $V_\beta 15$ | Seq ID No. | CDR3 Region | Seq ID No. | $J_\beta$ | CDR3 Size (aa) |
|---|---|---|---|---|---|---|---|
| 07210601- clone No. 11 | 1 | CAT | 20 | YPGLADNEQF | 39 | FGPGTRLT 2.1 | 10 |
| 07210601- clone No. 12 | 2 | CAT | 21 | YPGLADNEQF | 40 | FGPGTRLT 2.1 | 10 |
| 07210601- clone No. 13 | 3 | CAT | 22 | YPGLADNEQF | 41 | FGPGTRLT 2.1 | 10 |
| 07210601- clone No. 14 | 4 | CAT | 23 | YPGLADNEQF | 42 | FGPGTRLT 2.1 | 10 |
| 07210601- clone No. 15 | 5 | CAT | 24 | YPGLADNEQF | 43 | FGPGTRLT 2.1 | 10 |
| 07210601- clone No. 16 | 6 | CAT | 25 | YPGLADNEQF | 44 | FGPGTRLT 2.1 | 10 |
| 07210601- clone No. 17 | 7 | CAT | 26 | YPGLADNEQF | 45 | FGPGTRLT 2.1 | 10 |
| 07210601- clone No. 18 | 8 | CAT | 27 | YPGLADNEQF | 46 | FGPGTRLT 2.1 | 10 |
| 07210601- clone No. 19 | 9 | CAT | 28 | YPGLADNEQF | 47 | FGPGTRLT 2.1 | 10 |
| 07210601- clone No. 20 | 10 | CAT | 29 | YPGLADNEQF | 48 | FGPGTRLT 2.1 | 10 |

| Clones | Seq ID No. | $V_\beta 15$ | Seq ID No. | CDR3 Region | Seq ID No. | $J_\beta$ | CDR3 Size (aa) |
|---|---|---|---|---|---|---|---|
| 08030601- clone No. 31 | 11 | CAS | 30 | SPTGNEQF | 49 | FGPGTRL 2.1 | 8 |
| 08030601- clone No. 32 | 12 | CAS | 31 | SPTGNEQF | 50 | FGPGTRL 2.1 | 8 |
| 08030601- clone No. 35 | 13 | CAS | 32 | SPTGNEQF | 51 | FGPGTRL 2.1 | 8 |
| 08030601- clone No. 33 | 14 | CAS | 33 | SYNFGSNEKLF | 52 | FGSGTQL 1.4 | 11 |
| 08030601- clone No. 34 | 15 | CAS | 34 | SYNFGSNEKLF | 53 | FGSGTQL 1.4 | 11 |
| 08030601- clone No. 36 | 16 | CAS | 35 | SYNFGSNEKLF | 54 | FGSGTQL 1.4 | 11 |
| 08030601- clone No. 37 | 17 | CAS | 36 | SYNFGSNEKLF | 55 | FGSGTQL 1.4 | 11 |
| 08030601- clone No. 38 | 18 | CAS | 37 | SYNFGSNEKLF | 56 | FGSGTQL 1.4 | 11 |
| 08030601- clone No. 39 | 19 | CAS | 38 | SYNFGSNEKLF | 57 | FGSGTQL 1.4 | 11 |

Figure 5.

METHOD OF DIAGNOSING OR ASSESSING RISK FOR PARKINSON'S DISEASE OR ALZHEIMER'S DISEASE USING TCR CLONALITY

CROSS REFERENCE TO RELATED APPLICATION

This application claims priority to pending U.S. Provisional Patent Application No. 61/174,833, entitled "TCR Clonality as Marker for Alzheimer's Disease", filed on May 1, 2009, the contents of which are herein incorporated by reference.

FIELD OF INVENTION

This invention relates to amyloid beta screening. Specifically, the invention uses immune cell characteristics to screen for amyloid beta status.

BACKGROUND OF THE INVENTION

Alzheimer's disease (AD) is an age dependent disease and may include components of autoimmunity. Amyloid beta (Aβ), a peptide cleavage product of the amyloid precursor protein (APP), is a potentially immunogenic protein which may activate both T-cells and B-cells through their receptors. Some anti-Aβ antibodies have been detected in the blood of AD patients (Gaskin, et al. Human antibodies reactive with beta-amyloid protein in Alzheimer's disease. J Exp Med. 1993 Apr. 1; 177(4):1181-6; Gaskin, et al. Autoantibodies to neurofibrillary tangles and brain tissue in Alzheimer's disease. Establishment of Epstein-Barr virus-transformed antibody-producing cell lines. J Exp Med. 1987 Jan. 1; 165(1): 245-50). Anti-Aβ antibody therapy and T-cell treatment have shown benefit in APP mouse models and are being tested in patients (Monsonego & Weiner, Immunotherapeutic approaches to Alzheimer's disease. Science. 2003 Oct. 31; 302(5646):834-8; Morgan, et al. A beta peptide vaccination prevents memory loss in an animal model of Alzheimer's disease. Nature. 2000 Dec. 21-28; 408(6815):982-5; Ethell, et al., Abeta-specific T-cells reverse cognitive decline and synaptic loss in Alzheimer's mice. Neurobiol Dis. 2006 August; 23(2):351-61. Epub 2006 May 30; Wilcock, et al., Microglial activation facilitates Abeta plaque removal following intracranial anti-Abeta antibody administration. Neurobiol Dis. 2004 February; 15(1):11-20). One classic treatment for autoimmune disease, the injection of Intravenous Immunoglobulin (IVIg), has been reported to reduce cognitive problems in AD patients as well. Current diagnosis involves a series of cognition and/or motor function tests and medical history analysis. Some diagnoses of AD rely on the observation of Aβ and tau pathology in the brain, such as imaging technology designed to detect Alzheimer's plaques and tangles.

A vital part of the immune system's response is its ability to adapt to new challenges. One key feature of adaptive immunity is the presence of a highly diverse repertoire of antibodies (B-cell receptors) and T-cell receptors to identify neo-antigens associated with new immune challenges. This diversity is maintained largely by genetic recombination involving selective inclusion of one of the multiple V, D, and J gene segments of immunoglobulins (BCR) and TCRs within individual B-cells and T-cells, respectively.

TCRs are related to immunoglobulins (BCRs) in that the antigen binding domains are generated by somatic recombination during cell development, which shares high similarity. There are four gene loci for TcR, which undergo recombination during development. Unlike BCRs, the TCRs are mainly cell surface molecules with a single antigen recognition site (Janeway, Travers, Walport, Shlomchik, *Immunology*. (Garland Publishing, New York, ed. 5th, 2001). Most importantly, however, the TCR recognizes short peptide fragments from pathogens. Perhaps due to the MHC portion of the ligand, somatic hypermutation does not occur in TCR genes. Such mutations might result in the loss of recognition of the ligand (Slifka & Whitton, Functional avidity maturation of CD8(+) T-cells without selection of higher affinity TCR. Nat Immunol. 2001 August; 2(8):711-7). This is consistent with the proposal by Jerne (Jerne, The somatic generation of immune recognition. Eur J Immunol. 1971 January; 1(1):1-9) that the germ line antigen receptors are predisposed to react with MHC molecules.

T-cells produce two different TcRs, the αβTcR and the γδTcR. The αβTcR predominates, and consists of a heterodimer of α and β chains, each coded by different gene products. Both the α and β chain comprise two external Ig-like domains anchored into the plasma membrane by a transmembrane peptide and a short cytoplasmic tail. The heavy chain (variable) domain gene is assembled from a V gene encoding approximately the first 94 residues, which combines with a D (diversity) gene segment and a J (joining) gene segment. The region of the V-D-J junction forms the third hypervariable regions of the V domain, while the first and second hypervariable regions are encoded within the V gene. There are more than 200 V genes in the IgH locus, with 10 D genes and 4 J genes. Since any of the V genes can recombine with any D gene and any J gene, the number of possible combinations of V-D-J is enormous. Light chain genes also undergo recombination, but these loci only contain V and J gene segments, so the third hypervariable region of the light chain is formed at a V-J junction. Recombination of either heavy or light chain genes leads to the loss of the intervening stretches of DNA, containing both introns and exons. Within the T-cell β-chain population, in addition to the diversity generated by the specific V gene fragment included in the TCR, there is internal deletion of portions of the V gene segment, creating length heterogeneity of the V domain in the final TCR. The loci contain VDJ and C gene segments, and somatic rearrangement must occur to generate a functional TcR gene. The rearrangement process generates most of the diverse range of receptors required to mount an effective immune response.

The ability of V, D, and J gene segments to combine together randomly introduces a large element of combinatorial diversity into the Ig and TcR repertoires. The precise point at which V, D, and J segments can join vary, giving rise to local amino acid diversity at the junction. The exact nucleotide position of joining can differ by as much as 10 residues resulting in deletion of nucleotides form the ends of the V, D, and J gene segments. During the rearrangement process additional nucleotides not encoded by either gene segment can be added at the junction between the joined gene segments, called "N-region diversity".

Motz, et al. reported that cigarette smoke can drive TCR clonality in a tissue specific manner in mice (Motz, et al. Persistence of lung CD8 T-cell oligoclonal expansions upon smoking cessation in a mouse model of cigarette smoke-induced emphysema. J Immunol. 2008 Dec. 1; 181(11):8036-43). Motz also reported that the 'restricted' versatility of the TCR in contrast to the BCR might serve a homeostatic function. In this way, the subtly variable T-cells constitute an evolutionary link between the invariable innate and hypervariable B-cell systems. Consistent with this notion, 5-8% of the notoriously heterogeneous neutrophil population (at least 18 subsets) carry a TCR-based variable immunoreceptor (Puellmann, et al. A variable immunoreceptor in a subpopulation of human neutrophils. Proc Natl Acad Sci USA. 2006 Sep. 26; 103(39):14441-6. Epub 2006 Sep. 18). Some of these neutrophils are totally inactive and have strikingly different surface properties (Eggleton, et al. Fractionation of human neutrophils into subpopulations by countercurrent distribution: surface charge and functional heterogeneity. Eur J Cell Biol. 1992 April; 57(2):265-72). Bakács, et al also earlier suggested a model in which a dynamic steady state neutrophil population was achieved by interactions between T-cells and host cells (Bakács, et al. Some aspects of complementarity in the immune system. A bird's eye view. Int Arch Allergy Immunol. 2001 September; 126(1):23-31).

However, the immune system declines with increasing age, starting at around 50 years of age in humans, through immunosenescence. T-cells change in both number and function with the atrophy of the thymus, when T-cells mature. The human immune system maintains a so-called 'blind homeostasis' since it senses all CD3 T-cells. As the number of soluble TCRs is reduced due to the destruction of T-cells, more and more membrane-bound pMHC molecules become free. This generates a feedback homeostatic regulatory signal from complementary cells in tissues, which stimulate T-cell production and recruitment. It is also postulated that the peptide recognized by the helper T-cells should be a physical part of the antigen, which is recognized by the B-cell. Such a peptide is produced by the internalization of the BCR-bound antigen (Janeway, Travers, Walport, Shlomchik, *Immunology*. (Garland Publishing, New York, ed. 5th, 2001). Therefore, both B-cells and T-cells are involved in homeostasis and disease progression.

Current AD diagnosis relies on the observation of Aβ and tau pathology in the brain. Previous biomarker screenings for AD were cross-sectional studies and focused on plasma cytokine levels which are easily affected by acute injury. However, new diagnosis methods for AD, particularly in blood, are desperately needed for early diagnosis and initiation of treatment.

SUMMARY OF THE INVENTION

There has been considerable focus on the innate component of the immune system, with many lines of evidence suggesting that enhanced inflammatory reactions may contribute to AD pathogenesis. Therefore, some therapeutic approaches have been developed to target excessive innate immune system activation. However, changes in adaptive immunity have been studied haphazardly and typically in small cohorts. Few studies have focused on the relationship of peripheral immune system activity and pathological change in AD, especially regarding B-cell and T-cell diversity. Moreover, longitudinal analysis of immune system activity has rarely been studied with regards to AD diagnosis and prognosis. The present study compares T-cell and B-cell impairment associated with AD progression.

The distribution of T-cell and B-cell populations, plasma immunoglobulin (Ig) isotyping, and T-cell and B-cell receptor gene (membrane bound antibody) changes was analyzed as markers for AD diagnosis and prognosis. Total mature B-cells were detected with flow cytometry among normal, mild cognitive impairment (MCI), and AD patients. B-Cell Receptor (BCR) and T-Cell Receptor (TcR) CDR3 chains were amplified by RT-PCR and the diversity evaluated as for TCR5. Luminex technology used for plasma Ig isotyping and measurement of plasma levels of both $A\beta_{40}$ and $A\beta_{42}$.

The present invention provides a novel means to identify changes in adaptive immune system function as a predictor of neurodegenerative disease progression, such as AD, through the isolation of immune cells from an individual. Based on the data collected from the Florida ADRC samples, the peripheral immune system was analyzed to address whether immune alterations can serve as markers for AD progression. It is contemplated that the immune cells are T-cells, B-cells, or combinations thereof from the individual. Nucleic acids are isolated from the isolated immune cells, as is known in the art, corresponding to the CDR3 region, and the CDR3 region amplified. The amplified CDR3 fragments were then separated by length, providing an intrafamily gene fragment length profile for the CDR3 region. This intrafamily gene fragment length profile may then be compared to controls, thereby indicating the existence of a neurodegenerative disease.

The profiles preferably show the clonality of the CDR3 region, through analysis of the presence or an absence of at least one gene fragment length that is more prevalent in the assay profile, i.e. a banding pattern. T-Cell Receptor (TCR) diversity was also measured using an RT-PCR assay for all TCR Vβ chains to detect development of clonality (loss of diversity) in normal, MCI and AD patients. Control profiles may be compiled as an averaged profile derived from a plurality of single TCR-CDR3 intrafamily gene fragment length profiles, and wherein each of said single profiles is derived from blood cells of a healthy, age-matched human subject. In certain embodiments, the CDR3 region analyzed encompasses 22 Vβ families, however it has been found that Vβ 7, 8, 9, 10, 11, 12, 13, 14, 15, 16, 17, 18, 20, 21, and combinations thereof are useful in the invention. As noted above, the novel method is useful in diagnosing neurodegenerative disease, like Parkinson's disease or Alzheimer's disease. Moreover, this permits the clinical identification of patients at a very early stage of AD and/or monitoring the potential benefits of disease modifying therapeutics.

Advantageously, the method may be performed using nucleic acids, such as mRNA, DNA, and cDNA. Where mRNA is used, the method allows for use of polymerase chain reaction to generate complementary DNA (cDNA) from the mRNA, for example through use of RT-PCR. In a specific embodiment, the complimentary DNA encodes for Vβ region of CDR3.

Immune cells may be collected by means known in the art, such as collection of peripheral blood sample from an individual, and isolation of the immune cells present within the sample. The immune cells may then be selectively isolated using a cytokine or cell marker, like $CD4^+$, $CD8^+$, $CD5^+$, or $CD27^+$ by means such as magnetic cell sorting. The relative proportion of T-cell populations, T-cell function and loss of T-cell receptor (TCR) diversity was analyzed as markers for AD diagnosis and prognosis. Flow cytometry is used to analyze CD3, CD4, CD8, and CD25 populations in blood, and ELISpot assays to detect T-cell function by reaction to mitogen.

BRIEF DESCRIPTION OF THE DRAWINGS

For a fuller understanding of the invention, reference should be made to the following detailed description, taken in connection with the accompanying drawings, in which.

Figure 2:
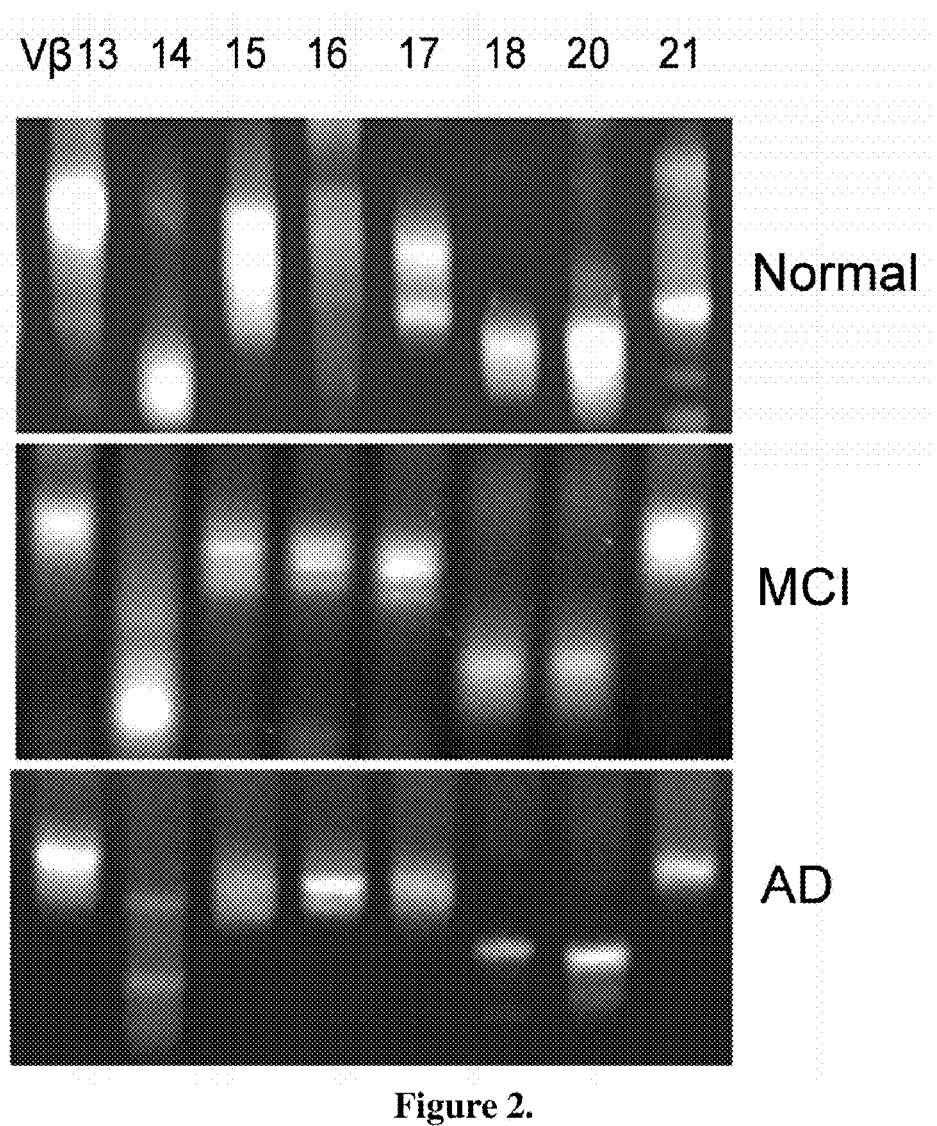

FIG. 2 is a series of blots showing changes in Vβ segment clonality in CD8+ T-cells from Normal, MCI and AD patients (note segments 18, 20 and 21 in the AD case).

Figure 3:
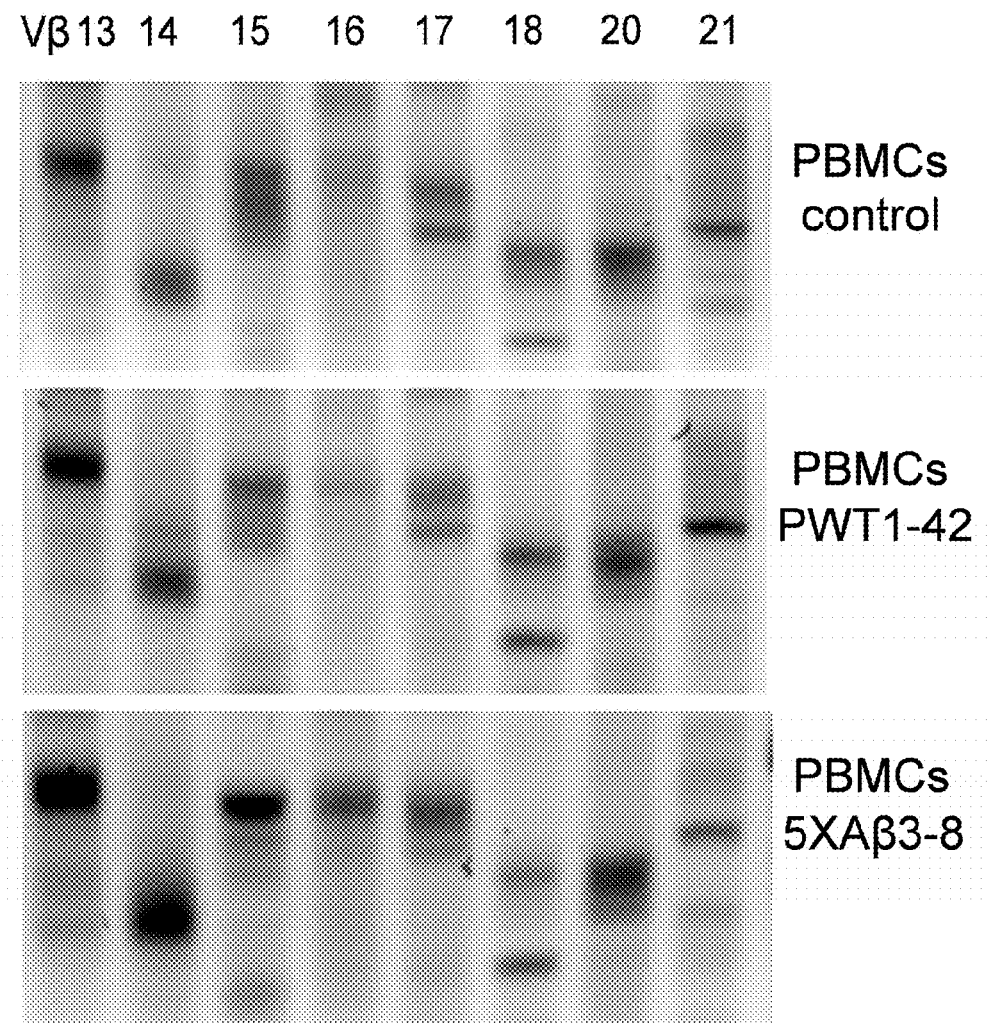

FIG. 3 is a series of blots showing changes in the CD8+ T-cell Vβ segment repertoire is shown before and after peptide stimulation in a young normal patient stimulated overnight with medium (upper), full length AR (middle), or a peptide consisting of 5 copies of Aβ3-7 (bottom) (there is a noticeable response with Vβ15).

Figure 4:
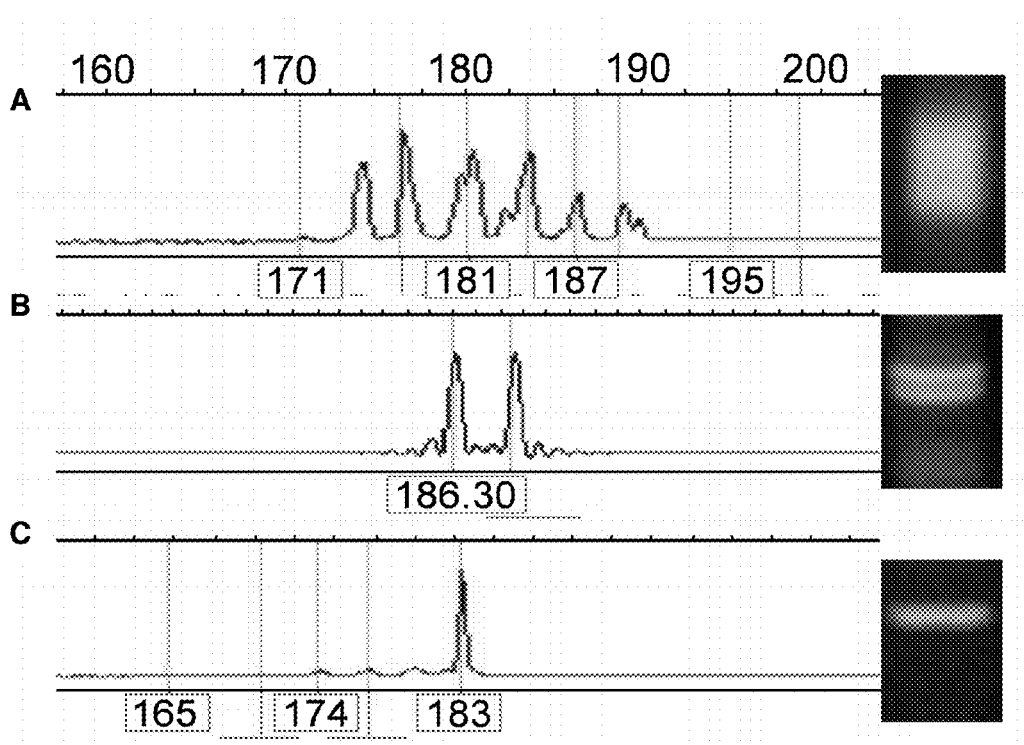

FIGS. 4(A) through (C) are genescan results for PCR products. The graphs are illustrations of the size of PCR products evaluated by Genescan rather than gel electrophoresis. (A) A genescan of Normal Vβ15 demonstrating conditions without clonality, because there are multiple peaks representing variable sizes of PCR products. (B) A genescan of AD Vβ13 demonstrating that a biclonal response occurred, because there are two peaks representing two sizes. (C) A genescan of AD Vβ15 representing a clonal condition with reduced diversity at that Vβ segment. Corresponding agarose gel images are shown to the right of the Genescan analysis.

FIG. 5 is a table showing the sequencing results for both monoclonal and oligoclonal TCRs. TCR Vβ15 (top section) and Vβ13 (bottom section) bands were excised from agarose gels after RT-PCR and cloned into a TA-vector. Ten clones from each transformant were picked and submitted for gene sequencing of the CDR3 region, then translated into the amino acid sequence. Vβ13 has two sequences as shown in panel B (oligoclonal) and Vβ15 has only one sequence as shown in panel A (monoclonal).

Figure 6:
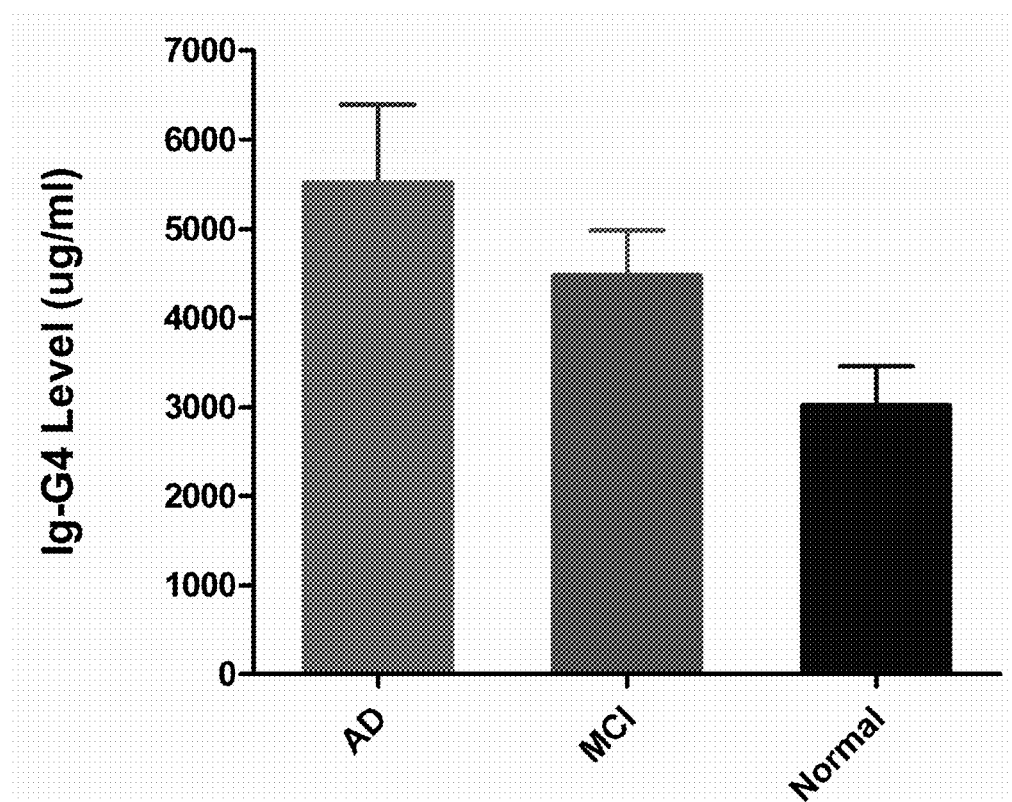

FIG. 6 is a graph showing plasma immunoglobulin levels for Normal, MCI and AD patients. Plasma samples were randomly collected and analyzed from the Tampa site of the FADRC for immunoglobulin Immunoglobulin levels were measured with the Ig isotyping assay (Millipore, Mass.), and total IgG4 levels show a trend to increase with disease progression ($0.1 > p > 0.05$).

Figure 7:
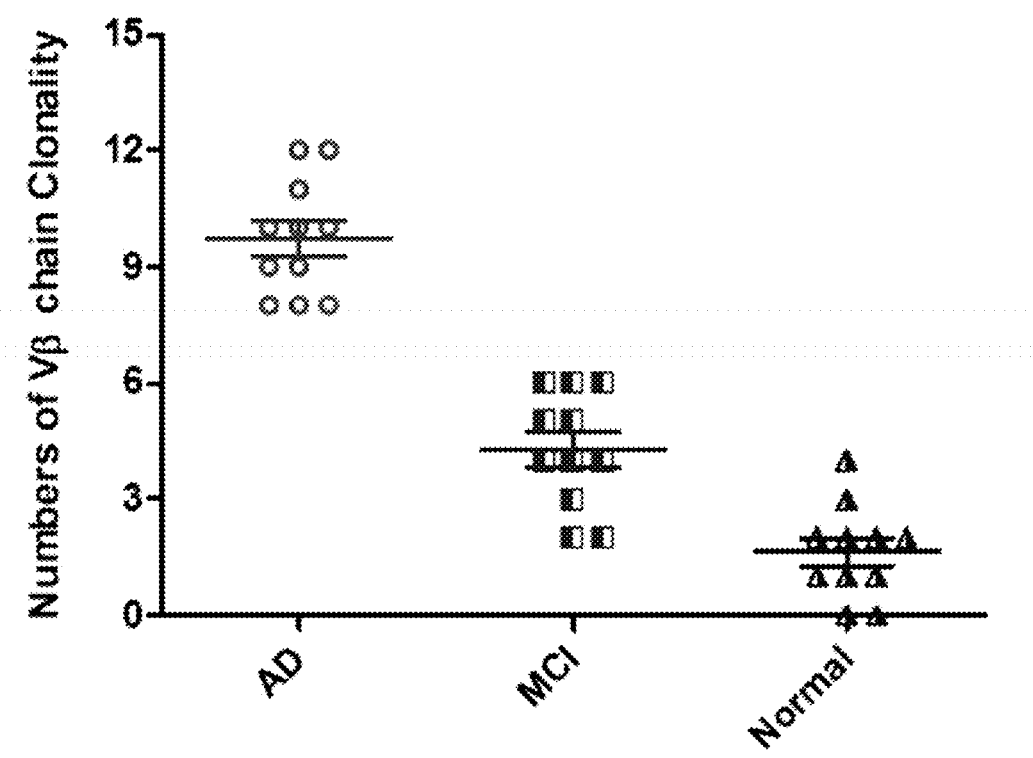

FIG. 7 is a graph showing the distribution of Vβ chain clonality numbers to disease progression. Normal, MCI and AD patient clonalities were plotted. There is significantly more TCR clonality occurring in AD than in MCI samples and also significantly more in MCI than normal samples.

Figure 8:
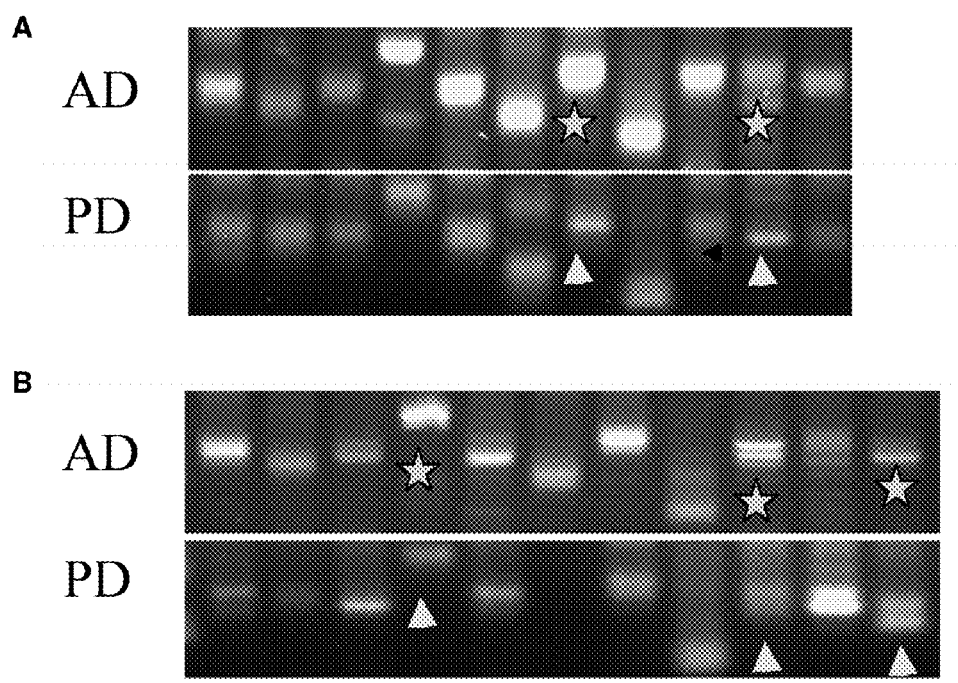

FIGS. 8(A) and (B) are a series of blots showing changes in Vβ segment clonality. (A) CD4+ T Vβ 6-17 chains were compared for AD and PD cases. There is significant clonality in PD patients. (B) CD8+ Vβ 6-17 TCR from AD and PD patients. Both cases exhibit clonality of TCR receptors but the pattern of clonality in PD differs from AD. Single thin bands showing clonality are indicated by arrows, whereas broad smears are indicated by stars.

DETAILED DESCRIPTION OF THE PREFERRED EMBODIMENT

AD is a neurodegenerative disease, characterized by Aβ peptide deposition in the brain, whose prevalence increases with aging. Therefore age is regarded as the major risk factor for AD. However, Aβ is a potentially immunogenic peptide existing in the blood, which is also prone to aggregation, and forms higher molecular structures which have the potential to trigger immune responses to intermolecular epitopes (conformations rather than sequences) and break immune tolerance. Therefore, this study focuses on whether circulating Aβ interacts with T-cells and B-cells, leading to a change of immune function.

The term "individual" includes mammals and non-mammals. Non-limiting examples include humans, non-human primates, species of the family bovidae, species of the family suidae, domestic animals including rabbits, dogs, and cats, laboratory animals, such as rats, mice, guinea pigs, and non-mammals, including birds and fish.

The term "cell sorting" means a method of selectively isolating specific populations of cells, such as those described by Yen, et al. (U.S. Pat. No. 4,219,411); MacMichael, et al. (U.S. Pat. No. 5,914,262); Schindler, et al. (U.S. Pat. No. 4,624,915); Diessel, et al. (U.S. Pat. No. 5,837,200); Josephson (U.S. Pat. No. 4,672,040). These methods and systems are exemplary only and not intended to limit the scope of the invention. Cell sorting procedures include affinity separation, such as affinity column, batch elution, fluorescence activated cell sorting, magnetic cell sorting, Magnetic-activated cell sorting (MACS) (Miltenyi Biotec GmbH Germany), and magnetic beads (Life Technologies, Inc., Carlsbad, Calif.). These methods may be used to positively select a population, i.e. collecting the population of interest, or to negatively select a population, i.e. selectively removing populations from a liquid until only a population of interest remains.

The term "nucleic acid" means an unbranched polynucleotide chain, in which the 5' phosphoric group of each nucleotide is esterified with the 3' hydroxyl of the adjoining nucleotide. The term includes, without limiting the scope of the invention, deoxyribonucleic acid (DNA), ribonucleic acid (RNA), and complimentary DNA. The nucleic acid can be either single-stranded or double-stranded molecules, gene expression constructs, and similar molecules. The term also includes analogs, derivatives, and constructs that include promoter, leader, signal, intron sequences, and control regions.

The term "separating by length" means subjecting nucleic acids to any method by which DNA molecules can be separated based on size, charge, length, structure, or combination thereof, such that the results permit comparison of molecules present or absent in a sample. The separation may be by electrophoretic or chromatographic means, such as any non-denaturing cathodic or anodic electrophoresis including sodium dodecyl sulfate electrophoresis. Gel electrophoresis, using for example agarose or polyacrylamide, is a convenient separation technique which may be used with the present invention.

The term "CDR" means a portion of a polypeptide encoding non-contiguous antigen combining sites found within the variable regions of both heavy and light chain polypeptides. The exact amino acid residues which encompass a specific CDR will vary depending on the structure of the CDR, which comprise a hypervariable region and/or a region containing amino acids which maintain conformation of the binding loops of the polypeptide which defines specificity and affinity to an antigen or target. One variant CDR is CDR3, the third complementarity-determining region of TCR which interacts directly with antigenic peptides bound to grooves of MHC molecules (Nishio, et al. Development of TCRB CDR3 length repertoire of human T lymphocytes. Int Immunol. 2004 March; 16(3):423-31). One of ordinary skill in the art may determine the regions comprising CDR sequence, as defined by Kabat, et al. Sequences of Proteins of Immunological Interest, 1991.

The term "neurodegenerative disease" means a central nervous system disorder characterized by progressive loss of functional neural tissue. Of particular interest is the treatment of neurodegenerative diseases in which the afflicated patient has activated immune cells. Exemplary neurodegenerative diseases include HIV-associated dementia (HAD), Alzheimer's disease, and Parkinson's disease.

The peripheral immune system and the immune system in the brain interact with each other (Solomon, Psychoneuroimmunology: interactions between central nervous system and immune system. J Neurosci Res. 1987; 18(1):1-9). For example, CD4 and CD8 cells have been identified in the brain of AD patients (Rogers, et al. Expression of immune system-associated antigens by cells of the human central nervous system: relationship to the pathology of Alzheimer's disease. Neurobiol Aging. 1988 July-August; 9(4):339-49). This led to the hypothesis that immunological aberrations in AD may manifest themselves in peripheral immune reactions (Antonaci, et al. Senile dementia, Alzheimer type: a distinct entity in the immunosenescence? J Clin Lab Anal. 1990; 4(1):16-21). Differences in the overall distribution of T-cell subtypes has been discovered in AD compared to normal control subjects (Antonaci, et al. Senile dementia, Alzheimer type: a distinct entity in the immunosenescence? J Clin Lab Anal. 1990; 4(1):16-21; Richartz-Salzburger, et al. Altered lymphocyte distribution in Alzheimer's disease. J Psychiatr Res. 2007 January-February; 41(1-2):174-8. Epub 2006 Mar. 3), but there are no differences in total number of PBMCs (Otsuka, et al. Rapid appearance of beta-amyloid precursor protein immunoreactivity in damaged axons and reactive glial cells in rat brain following needle stab injury. Brain Res. 1991 Dec. 24; 568(1-2):335-8; Singh, Immune-activation model in Alzheimer disease. Mol Chem Neuropathol. 1996 May-August; 28(1-3):105-11). T-cells are activated in response to stimulation through their surface receptor (TCR) while encountering antigen. A number of soluble proteins corresponding to the extracellular portions of transmembrane receptors have now been identified in biological fluids (Contini, et al., Soluble HLA-A, -B, -C and -G molecules induce apoptosis in T- and NK CD8+ cells and inhibit cytotoxic T-cell activity through CD8 ligation. Eur J Immunol. 2003 January; 33(1):125-34; Ishizaka &. Tsujii, Soluble T-cell products antigenically related to T-cell receptors. Cytokine. 1995 April; 7(3):260-6; Jinushi, et al. Therapy-induced antibodies to MHC class I chain-related protein A antagonize immune suppression and stimulate antitumor cytotoxicity. Proc Natl Acad Sci USA. 2006 Jun. 13; 103(24):9190-5. Epub 2006 Jun. 5). Thus, immune and non-immune cells may also communicate via the soluble form of their cell surface molecules. They may act either as antagonists or agonists in the regulation of general cellular homeostasis and in orchestrating immune responses during disease (Jones & Rose-John, The role of soluble receptors in cytokine biology: the agonistic properties of the sIL-6R/IL-6 complex. Biochim Biophys Acta. 2002 Nov. 11; 1592(3):251-63).

A vital part of the immune system's response is its ability to adapt to new challenges, namely through the somatic recombination of TCR and BCR genes. However, the immune system declines with increasing age, starting at around 50 years of age in humans, through immunosenescence. Thymus atrophy reduces the number of soluble TCRs due to the destruction of T-cells, causing more membrane-bound pMHC molecules become free and generating a feedback homeostatic regulatory signal from complementary cells in tissues, which stimulate T-cell production and recruitment. The immune system is dynamically interconnected with host cells through complementary TCR-MHC interactions (Bakács, et al. T cells survey the stability of the self: a testable hypothesis on the homeostatic role of TCR-MHC interactions. Int Arch Allergy Immunol. 2007; 144(2):171-82. Epub 2007 May 30). Matzinger (Matzinger, The danger model: a renewed sense of self. Science. 2002 Apr. 12; 296 (5566):301-5) suggested 'the possibility that immunity is controlled by an internal dialogue between tissues and the cells of the immune system'. Inflammation induces the coordinated up-regulation of the MHC antigen-presenting machinery, via an extensive interface between innate and acquired immune response (Yoo & Desiderio, Innate and acquired immunity intersect in a global view of the acute-phase response. Proc Natl Acad Sci USA. 2003 Feb. 4; 100 (3):1157-62. Epub 2003 Jan. 22). Evidence for self antigens (Ag) driving clonal expansions comes from the demonstration that elastin-reactive T-cells and antibodies exist in patients with COPD (Thimme et al., Determinants of viral clearance and persistence during acute hepatitis C virus infection. J Exp Med. 2001 Nov. 19; 194(10):1395-406). An alternative hypothesis is that persistent oligoclonal expansions of CD8 T-cells may be a generalized response to potent antigenic stimulation, and not the result of an active process. It has been demonstrated in mice that the peripheral CD8 T-cell repertoire can remain oligoclonal up to 7 months after one infection with lymphocytic choriomeningitis virus (Dillon & Root-Bernstein, Molecular complementarity II: energetic and vectorial basis of biological homeostasis and its implications for death. J Theor Biol. 1997 Oct. 21; 188(4):481-93).

Due to the existence of self-antigen and the fact that auto-antibodies are present in AD, it is believed that both a B-cell and T-cell immune response participate and contribute to AD progression. B-cell impairment with aging has been well explored (Weksler & Szabo, The effect of age on the B-cell repertoire. J Clin Immunol. 2000 July; 20(4):240-9; Breitbart, et al., Altered memory B-cell homeostasis in human aging. J Gerontol A Biol Sci Med Sci. 2002 August; 57(8): B304-11). The B-cell repertoire changes with age (Weksler & Szabo, The effect of age on the B-cell repertoire. J Clin Immunol. 2000 July; 20(4):240-9; Colonna-Romano, et al., B cell immunosenescence in the elderly and in centenarians. Rejuvenation Res. 2008 April; 11(2):433-9). The natural decline of the immune system affects both T- and B-cell function, and the toxicity of aggregated Aβ further impairs this function.

TCRs consist of a heterodimer of alpha and beta chains, each coded by different gene products. Within the T-cell β-chain population, in addition to the diversity generated by the specific V gene fragment included in the TCR, there is internal deletion of portions of the V gene segment, creating length heterogeneity of the V domain in the final TCR. Clones within a Vα or Vβ family consist of amino acid (AA) chains with multiple lengths. The AA length does not have a one-to-one relationship to a specific clone, but all cells of one clone share the same AA length. As a result, RT-PCR of a single Vβ-chain gene family segment from T-cell mRNA will typically result in a broad band on agarose gels, representing the diversity of length variants of that Vβ-chain segment, as seen FIG. 1 panels A and B).

The clonality assays in 22 TCR Vβ families was performed using TCRExpress Clonality Detecting and Quantitation Kit (BioMed Immunotech, Tampa, Fla.). Multiple PCR primer sets for each gene family composed of specific Vβ, Dβ, and Jβ primers were used to amplify products from total RNA from 0.2-2×10$^6$ purified T-lymphocytes to PCR plate I and II. For clonality detection analysis, the PCR products were completely separated by electrophoresis in a 4% high resolution gel (Bio-Rad). For quantitative analysis, the PCR products were further assayed using DNA analyzer and statistical software (BioMed Immunotech, Tampa, Fla.). Monoclonal T cells show a single defined band, while polyclonal T cells, such as those of cord blood, display a smear with no defined bands. GeneScan analysis for both TCR and BCR were conducted by labeling all forward PCR primers at the 5' end with a blue fluorescent dye (6-FAM). Fluorescent PCR products and a size marker (ROX400; Perkin-Elmer Biosystems, Foster City, Calif.) were mixed with formamide and were denatured at 94° C. for 2 mins. Samples were loaded onto a 6% acrylamide sequencing gel (National Diagnostic, Atlanta, Ga.) on a 96-lane Applied Biosystems model 3730 DNA sequencer and were run for 1.5 h. The data were analyzed and quantified by using ABIPRISM GeneScan analysis software, which calculates the relative intensity of each product generated.

EXAMPLE 1

Figure 1:
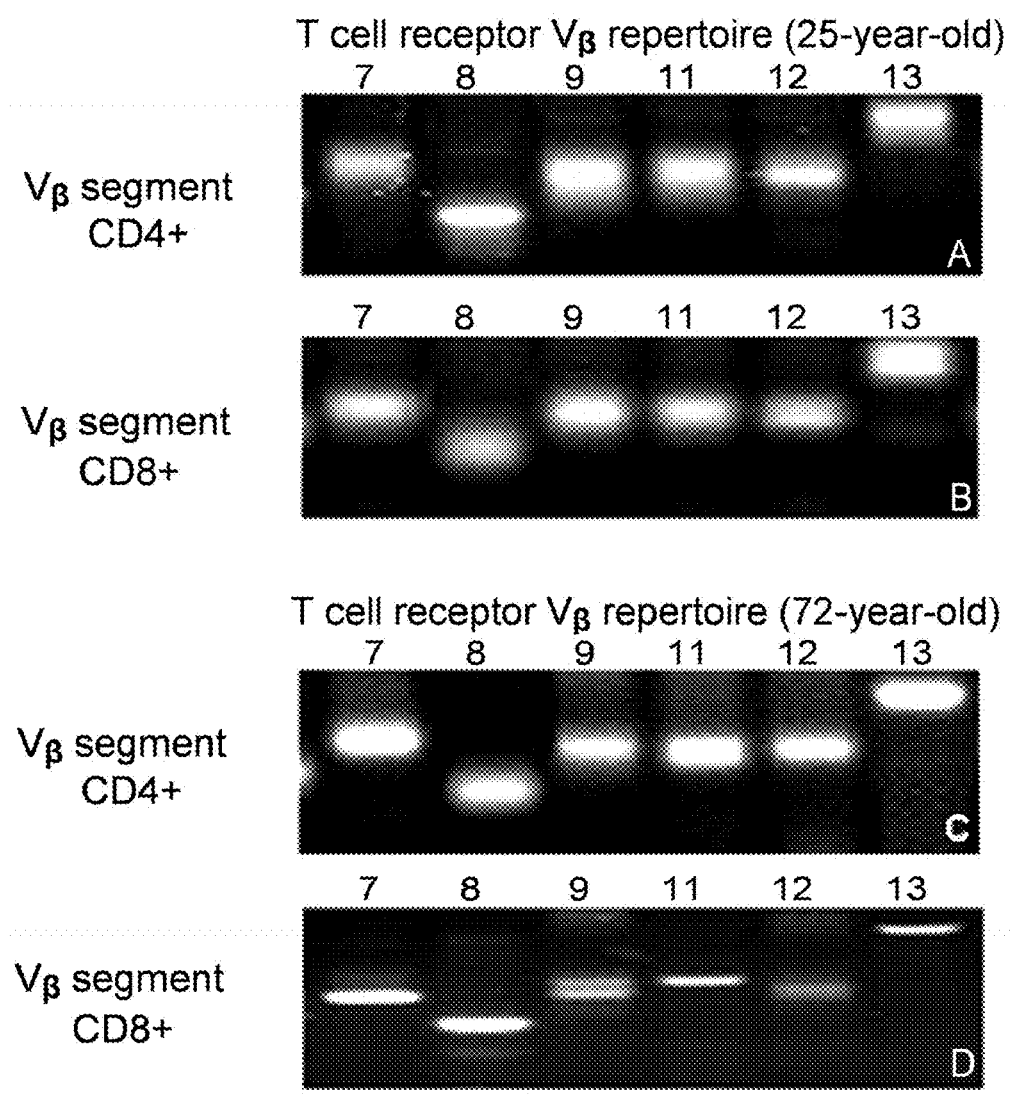
FIG. 1 is a series of blots showing the clonality assessment of 6 TCR-VB gene segments in a young and old individual. mRNA for both $CD4^+$ (A and C) and $CD8^+$ (B and D) cells were isolated and analyzed by RT-PCR for individual Vβ segments. Numbers 7 through 13 represents different Vβ segments. Reduction in band width or formation of doublets indicates restriction of the length heterogeneity and a decrease in diversity of the TCRs expressed in that CD8+ T cell population (compare D with B).

Twenty-two distinct human Vβ gene family segments were amplified and evaluated for length heterogeneity of the Vβ segments within T-cell samples from the ADRC, as well as in young and aged controls samples. In both $CD4^+$ and $CD8^+$ T-cell populations, normal length heterogeneity was identified for all 22 Vβ chain gene segments; 6 of which are represented in FIG. 1; in samples from young control blood, as seen in FIGS. 1(A) and (B). With age, length heterogeneity was maintained in the $CD4^+$ T-cells, but in general was reduced in the $CD8^+$ T-cell subset, as seen in the more discrete banding pattern in FIG. 1D compared to FIG. 1B; segments 11 and 13 would be scored as having restricted length diversity. This increase in clonality (decrease in heterogeneity) implies that the repertoire of this Vβ chain has decreased. This type of reaction can be seen after severe immune challenge such as vaccination or disease, when the T-cell population selectively expands those clones which are directed against the challenge. Thus, a restriction in length heterogeneity implies an impaired immune response secondary to a less diverse repertoire of TCRs to ward off new immune challenges. BCR kits, including PCR primers and information on their utility in assessing TCR diversification, were used to test for B-cell clonality detection (Biomed Immunotech, Tampa, Fla.).

In AD cases there is less Vβ segment diversity than in aged-matched control cases. In FIG. 2, the age matched control case (top) has considerable length heterogeneity compared to the AD case (bottom), with the MCI case being in between these two conditions (note in particular Vβ segments 18 and 20). In an initial set of cases, these differences were highly significant, with considerably less length heterogeneity (diversity) in the $CD8^+$ TCRs than the normal cases, and the MCI cases were intermediate between these two, as seen in FIGS. 6 and 7.

Given the antigenicity of Aβ, it was also investigated whether this antigen might stimulate clonality of Vβ segments. PBMCs were incubated overnight with either medium, full length $Aβ_{1-40}$, or a repeating peptide consisting of 5 copies of the Aβ3-7 sequence (a major antigenic determinant in vaccine preparations (Dickey et al., Duration and specificity of humoral immune responses in mice vaccinated with the Alzheimer's disease-associated beta-amyloid 1-42 peptide. DNA Cell Biol. 2001 November; 20(11):723-9). It was noted that for VR segment 15, there was an increase in clonality, seen in the bottom of FIG. 3, compared to the control condition, seen in the top of FIG. 3, with the full length peptide having an intermediate response. This is consistent with T-cell activation and expansion of a $CD8^+$ T-cell that reacted to the AR antigen and increased its representation within the T-cell population.

The PCR products were analyzed by genescan to quantitatively determine expression. Exemplary results are shown in FIGS. 4(A)-(C), indicating the type of results found for normal, heterogeneous cells, shown in FIG. 4(A) with multiple peaks representing variable sizes of PCR products. As the cells become stimulated, by an antigen or Aβ peptide, the cells increase in clonality, seen in FIG. 4(B) showing a biclonal response. Finally, the cells loose hetergenicity, becoming clonal, as seen in FIG. 4(C). Of important note, contacting T-cells with AD Vβ15 resulted in a clonal condition with reduced diversity at the Vβ segment.

CDR3 sequences suggest Ag-driven T-cell oligoclonal expansion. To determine whether the dominant CDR3 spectratype peaks corresponded to shared CDR3 amino acid motifs, thus indicating traditional Ag-driven clonal expansions, nucleic acid sequencing was performed on these CDR3 regions, as seen in FIG. 5. Moreover, preferential usage of CDR3 lengths in the same Vβ of different mice strongly suggested Ag-driven oligoclonal expansions (Motz, et al. Persistence of lung CD8 T cell oligoclonal expansions upon smoking cessation in a mouse model of cigarette smoke-induced emphysema. J Immunol. 2008 Dec. 1; 181(11):8036-43), which is further supported by the nucleic acid sequence data from others demonstrating dominant clones with highly similar β-chain CDR3 sequences within individual cigarette smoke-exposed mice. It is likely that there are common Ag's driving oligoclonal expansions in the disclosed model, because of the presence of both identical and highly similar clones present in several different cigarette smoke-exposed mice.

EXAMPLE 2

Subjects having NCI, MCI, or AD were recruited into the clinical core received a full diagnostic evaluation, as required by the National Alzheimer's Coordinating Center (NACC), and classified as normal, having Mild Cognitive Impairment (MCI), or as having dementia, according to NACC standardized protocols. In addition, MCI cases were further classified according to the predominant cognitive feature (amnestic, non-amnestic), as well as the number of cognitive domains that are affected (single vs. multiple). Finally, the differential diagnoses are provided for the dementia cases. Initial diagnosis showed 135 persons as having dementia, with 121 of those classified as probable or possible AD. As for MCI, 132 were classified as having the amnestic variety, whereas 77 were classified as non-amnestic. Finally, 261 individuals were classified with normal cognitive performance (NCI), and another 209 individuals were described by a more recent NACC classification of Impaired-Not MCI.

Blood was drawn (30 ml) with an EDTA tube and delivered to the lab within 24 hours. Two ml of whole blood were aliquoted into a new tube for the flow cytometry assay to analyze CD3, CD4, CD8 and CD25 markers for T-cells as well as CD5, CD19 and CD27 markers for B-cells. The remaining whole blood was processed for plasma and PBMCs isolation by following a standard ficoll paque protocol. Isolated PBMCs were then separated and used for TCR analysis, BCR analysis, and T-cell stimulation. PBMCs were thawed or used fresh after isolation, cultured, and stimulated by Aβ peptide and PMA for 24 hours. Then the supernatant was collected for cytokine analysis. Cells were then separated for both CD4 and CD8, and TCR analysis.

$CD4^+$ or $CD8^+$ T-cell subsets were purified from isolated PBMCs or peptide stimulated PBMCs using magnetic microbeads coated with an anti-CD4 antibody or CD antibody (Invitrogen Corporation, Carlsbad, Calif.). The purity of each T-cell subpopulation was determined by flow cytometry until isolate purity was greater than 95%, and molecular analysis with less than 1% contamination with the reciprocal subpopulation.

The current literature argues that T-cell function is impaired with aging, and antigen stimulation plus aging may have additive effects on the diversity of TCR sequences. Different T-cell subtypes may be more or less affected due to the modifications in the microenvironment. CD4+, CD8+ were separated from total PBMCs using positive selection with a magnetic bead assay (Miltenyi Biotec Inc., Auburn, Calif., USA), and mRNA isolated for both cell types.

TCR Vβ repertoire clonality assays were conducted in 22 TCR Vβ families using TCRExpress Clonality Detecting and Quantitation Kit (BioMed Immunotech, Tampa, Fla.). In brief, PCR amplifications were performed by adding total RNA from $0.2-2 \times 10^6$ purified T-lymphocytes to PCR plate I and II. For clonality detection analysis, the PCR products were completely separated by electrophoresis in a 4% high resolution gel (Bio-Rad). For quantitative analysis, the PCR products were further assayed using DNA analyzer and statistical software (BioMed Immunotech, Tampa, Fla.). RT-PCR was performed with TCR Vβ chain detection kit (BioMed Immunotech, Tampa, Fla.) for all samples collected from year one and year five) and single PCR bands excised and cloned into a TA vector for sequencing for clone identification. Another analysis reviewed the antigen cell response to antigenic stimulation.

The TCR Vβ RT-PCR analysis has been applied to 33 samples from the human PBMC sample series, as seen in FIG. 7. These data reveal no overlap between the AD cases and the normal cases, with considerably greater numbers of Vβ sequences demonstrating clonality in the AD cases. MCI cases are intermediate between the two conditions with some overlap with the normal cases, but not AD. ANOVA and post hoc analysis demonstrates significant differences ($p<0.001$ for all group comparisons (AD>MCI>normal). In particular, the intermediate values for MCI samples indicate some capacity for predicting conversion to AD, versus those with stable MCI in the larger dataset when studied prospectively.

The mitochondrial membrane potential of each sub-population is analyzed with JC-1 by flow cytometry. For flow cytometry assays for T-cell population, 90 μl of whole blood is lysed with lysis buffer, and then washed twice with 1×PBS, followed by adding 250 microliters reading buffer and submitted for flow cytometery. Data is collected for each subject. For CD4, CD8 and T-reg analysis, whole blood is stained with CD4 (FITC, BD Pharmingen, Cat. No. 555346), and CD25 (PE, BD Pharmingen Cat. No. 555432) antibodies, then fixed for 10 min and permeabilized for 30 min using the BD Pharmingen Human FoxP3 buffer kit (BD Pharmingen Cat. No. 560098), and then stained with 20 μL/test of conjugated human FoxP3 (clone 259D/C7) antibody (BD Pharmingen Cat. Nos. 560046). The data were derived from an acquisition of 50,000 events in a lymphocyte gate, followed by CD4+ gating by fluorescence. Human FoxP3 Stain Kit-PE (contains FoxP3, CD4, CD25, and buffer set Cat 560133, BD Pharmingen) is used.

Participant immune responses to Aβ peptide and generic mitogen (PMA) stimulation are assayed using a human INF-γ ELISpot Kit (Cat#552138; BD Biosciences, San Jose, Calif.). In brief, PBMCs from human blood are seeded into a 96-well plate at $2 \times 10^5$ cells/well and stimulated with different Aβ peptide fragments at 10 μg/ml, or by R10 (negative control), PHA, or PMA (L9802, P8139 positive control, Sigma Alderich, St. Louis, Mo.). The cells are then incubated at 37° C. in a humidified tissue culture incubator with 5% $CO_2$ for 24 hours. After stimulation, plates are washed with nanopure water twice and washed with buffer 3 times. Biotinylated detection antibody is added and incubated for 2 hours at room temperature, followed by washing the plate with wash buffer 3 times, and streptavidin-HRP solution added. The plate is incubated for 1 hour at room temperature, and washed with wash buffer 4 times and washed with PBS twice, followed by addition of AEC Substrate solution. The plate is monitored for spot development for 5 to 60 minutes. The reaction is stopped by washing with nanopure water, and the plate air-dried at room temperature overnight. Spots are enumerated by using an ImmunoSpot image analyzer system (Cellular Technologies Limited, Cleveland, Ohio). Dimethyl sulfoxide is used as the negative control for the peptide pool (at same concentration present in EPI peptide pool antigen).

Because B-cell impairment is also age dependent, B-cells were isolated from PBMCs using CD5 and CD27 (B-cell isolation kits, Miltenyi Biotec Inc., Auburn, Calif., USA). The BCR is analyzed by RT-PCR. Also, the mitochondrial membrane potential of each sub-population was analyzed with JC-1 by flow cytometry. For flow cytometry assays for B-cell population, 90 μl of whole blood is lysed with lysis buffer and then washed twice with 1×PBS. 250 μl of reading buffer is added and the sample submitted for flow cytometery. Data is collected for each subject. For CD5, CD19 and CD27 analysis, whole blood is stained with mouse anti-Human CD5-FITC (BD Pharmingen, Cat. No. 551449), mouse anti-Human CD19-APC (BD Pharmingen, Cat. No. 555415), and mouse anti-human CD27-PE (BD Pharmingen, Cat. No. 555441) antibodies, fixed for 10 min, and then permeabilized for 30 min. The remaining procedures for data collection are identical to the T-cell flow cytometry, described above.

GeneScan analysis is conducted for both TCR and BCR. Forward PCR primers are labeled at the 5' end with a blue fluorescent dye (6-FAM). Fluorescent PCR products and a size marker (ROX400; Perkin-Elmer Biosystems, Foster City, Calif.) are mixed with formamide and denatured at 94° C. for 2 min. Samples are loaded onto a 6% acrylamide sequencing gel (National Diagnostic, Atlanta, Ga.) on a 96-lane Applied Biosystems model 3730 DNA sequencer and run for 1.5 h. The data are analyzed and quantified by using ABIPRISM GeneScan analysis software, which calculates the relative intensity of each product generated.

The PCR product bands of interest for both TCR and BCR are then excised for sequencing and purified using Micropure-EZ with Vial (Millipore, Billerica, Mass.) following the manufacturer's recommendations. Products are directly cloned into the TA cloning vector PCR 2.1 (Invitrogen Corporation, Carlsbad, Calif.), and sequenced using fluorescent dideoxy terminators, and analyzed on an Applied Biosystems Model 337A automated sequencer (Applied Biosystems, Foster City, Calif.). Sequencing of the CDR3 peptides are analyzed by using DNAMAN software (Lynnon Corporation, Pointe-Claire, PQ).

Cytokine expression profiles are detected using human cytokine Th1, Th2 and Th17 (Panomics, Fremont, Calif. 94555; Bio-rad Bio-Plex) kits according to the manufacturer's protocol. The concentration of each cytokine is calculated from a standard curve. Likewise, immunoglobulin in plasma is used to evaluate Th1 and Th2 responses, as well as evaluate B-cell function. Immunoglobulin subtype analysis was analyzed with Ig isotyping kit (Millipore, Billerica, Mass.) by using Luminex assay. Cytokines are considered useful as markers for inflammation.

Igs isotypes are analyzed by diluting plasma with sample diluents at 1:8000 (1×PBS contains 1.5% BSA), and incubated in a filter plate with beads (the Beadlyte® human Immunoglobulin Isotyping Kit by Upstate Cell Signaling Solutions (Temecula, Calif.)), strictly following the manufacturer's instructions. Each Ig isotype is calculated using a standard curve. Anti-Aβ antibody from all plasma samples is detected as described in Cao et al. (Cao, et al. Successful adjuvant-free vaccination of BALB/c mice with mutated amyloid beta peptides. BMC Neurosci. 2008 Feb. 18; 9:25). Plasma $A\beta_{1-40}$ and $A\beta_{1-42}$ level are detected simultaneously by using Luminex assay kits following the manufacture's protocol (Innogenetics, Inc. Alpharetta, Ga. 30004). Because AD is regarded as an inflammation-related disease, plasma cytokines for Th1, Th2 and Th17 (Panomics, Calif.) are analyzed by using Luminex to investigate if any one profile is dominant in AD or is associated with greater TCR or BCR clonality. In AD patients, total IgG and IgG4 show trends toward increasing with disease progression. This Ig level increase is likely due to auto-antibodies as reported by Gaskin (Gaskin, et al. Human antibodies reactive with beta-amyloid protein in Alzheimer's disease. J Exp Med. 1993 Apr. 1; 177(4):1181-6). The TCR expression repertoire significantly showed disease dependent clonality.

The mitochondrial membrane potential is monitored for B- and T-cell impairment in the cells by flow cytometry by the cationic (positively charged) dye JC-1 (5,5',6,6'-tetrachloro-1,1',3,3' tetraethylbenzimidazolylcarbocyanine iodide) (Invitrogen, Carlsbad, Calif.). The loss of mitochondrial membrane potential is a hallmark of apoptosis. In healthy cells, the dye forms aggregates in the mitochondria that fluoresce red. However in unhealthy cells with a lower mitochondrial membrane potential, the dye leaks out of the mitochondria into the cytoplasm as a monomer which fluoresces green. By comparing the ratio of red to green fluorescence by flow cytometry, the health of the mitochondria and the cells was assessed.

B-cell immunoglobulin heavy chain variable gene (IgH-V) repertoire (BCR) detection was designed to rapidly detect clonality of expanded B-cell population in CDR3 regions of the BCR. The method provides a RT-PCR-based gel assay for clonality detection of 9 IgH-V gene families, including IgH-V1.1, 1.2, 2, 3, 4.1, 4.2, 5, 6, and 7 in human B lymphocytes. In brief, total RNA is isolated from PBMCs, then one step screening PCR amplification (without cDNA initial synthesis step) is set up after RNA quantification. PCR products were analyzed with high resolution agarose gel followed with family specific PCR amplification. A successful PCR amplification displays a specific DNA band on the agarose gel from positive control and each sample (each IgH-V family) and no specific DNA band on negative well. DNA fragment size of the PCR products of 9 IgH-V gene families are between 100 to 220 bp. Clonality of the BCR repertoire is readily seen under UV light. Usually, there are three type repertoires observable in expanded T-cell populations. Monclonal repertoire—a single clear band; Oligoclonal repertoire—couple clear bands; Polyclonal repertoire—smear (similar as TCR).

Data was analyzed for sample sizes were based upon considerations of statistical power. In order to achieve statistical power of 0.80 with alpha level of 0.05, the effect for comparing the NCI vs. the AD groups must be at least 0.46. The smallest group difference was between the MCI and NCI groups and that standardized group difference in TCR Clones, as seen in FIG. 7, was 2.11 SD units. Thus, for mean differences the sample sizes proposed here are more than adequate. Data collected was subjected to a cross-sectional analysis.

The general analytic approach was to compare the T-cell values cross-sectionally for the three diagnostic groups (NCI, MCI, AD) to determine the ability of these values to differentiate the groups and then to examine the ability of these measures to predict incident cases of MCI and AD based upon longitudinal follow-up of the clinical cohort. The basic analytic approach to discriminate the three groups is to apply a multivariate GLM, after considering whether the groups also differ on basic demographic characteristics (e.g., age, gender, years of education). A relatively liberal criterion of alpha of 0.10 is used for the identification of covariates. To examine mean-level differences, diagnostic category is used as the IV and the T-cell measures as the DVs. In addition to examining group differences for those effects that are statistically significant, logistic regression analyses are applied that are designed to distinguish the cognitive impairment groups, following the application of relevant covariates.

EXAMPLE 3

The twenty-two distinct human Vβ gene family segments were amplified and evaluated as in Example 1, for testing of Parkinson's disease (PD). In both $CD4^+$ and $CD8^+$ T-cell populations, normal length heterogeneity was identified for all 22 Vβ chain gene segments; as seen in FIGS. 8(A) and (B). As noted above, length heterogeneity was maintained in the $CD4^+$ T-cells, but in general was reduced in the aged $CD8^+$ T-cell subset, as seen in the banding pattern of FIG. 1D compared to FIG. 1B, implying the Vβ chain has decreased. TCR kits, were used to test for T-cell clonality detection (Biomed Immunotech, Tampa, Fla.) in PD. As in AD, PD shows a decrease in Vβ segment diversity, though the banding patterns differ between the two diseases, as seen in FIGS. 8(A) and (B).

The data indicates that there is a loss of TCR and BCR diversity in the AD and PD cases and Ig isotyping changes with disease progress for at least AD and PD. Critically, the diversity must be correlated to age-normalized immune status to account for any excess of the normal age-related loss of diversity in the TCR, BCR and antibody repertoires as well as cytokine change. These observations are particularly valuable where the differences precede and predict conversion from normal or from MCI to more severe cognitive impairment. T-cell stimulation dynamics are also important in the $CD8^+$ population of T-cells which are less responsive than the $CD4^+$ population to antigen stimulation. Correlating these observations with the loss of Vβ chain diversity suggest mechanisms for this selective loss of stimulation.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of methods for the identification of neurological and neurodegenerative diseases, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of diagnosing or assessing risk for a neurodegenerative disease in an individual comprising the steps of:
   isolating immune cells, wherein the immune cells are T-cells, B-cells, or combinations thereof from the individual;
   isolating nucleic acids from the isolated immune cells, where the isolated nucleic acids encode for genes or proteins corresponding to the CDR3 region of the isolated immune cells;
   amplifying the CDR3 region of the nucleic acid;
   separating the amplified CDR3 fragments by length;
   determining a prevalence of the amplified CDR3 fragments to provide an intrafamily gene fragment length profile for the CDR3 region; and
   comparing the assay profile to a control intrafamily gene fragment length profile derived from blood cells of a healthy individual, to determine a presence or an absence of at least one gene fragment length that is more prevalent in the assay profile than the control profile, wherein the control profile is for the same TCR-CDR3 gene family as the assay profile; and wherein the presence of the more prevalent at least one gene fragment length CDR is indicative of the neurodegenerative disease;

wherein the neurodegenerative disease is Alzheimer's disease, Mild Cognitive Impairment, or Parkinson's disease.

2. The method of claim 1, wherein the nucleic acid is mRNA.

3. The method of claim 2, further comprising:
performing polymerase chain reaction to generate complementary DNA from the mRNA.

4. The method of claim 3, wherein the complementary DNA encodes for Vβ.

5. The method of claim 1, wherein the nucleic acid is DNA.

6. The method of claim 1, wherein the immune cells are selectively isolated using $CD4^+$, $CD8^+$, $CD5^+$, or $CD27^+$.

7. The method of claim 6, wherein the immune cells are isolated using magnetic cell sorting.

8. The method of claim 6, wherein the immune cells are selectively isolated using $CD8^+$.

9. The method of claim 1, wherein the neurodegenerative disease is Parkinson's disease, or Alzheimer's disease.

10. The method of claim 1, wherein the CDR3 region of the isolated immune cells encompasses 22 Vβ families, wherein the 22 Vβ families are selected from the group consisting of 7, 8, 9, 10, 11, 12, 13, 14, 15, 16, 17, 18, 20, and 21.

11. The method of claim 1, wherein the cells are derived from peripheral blood from the individual.

12. The method of claim 1, wherein the control profile is an averaged profile derived from a plurality of single TCR-CDR3 intrafamily gene fragment length profiles, and wherein each of said single profiles is derived from blood cells of a healthy, age-matched human subject.

13. A method of diagnosing or assessing risk for a neurodegenerative disease in an individual comprising the steps of:
isolating immune cells, wherein the immune cells are T-cells, B-cells, or combinations thereof from the individual;
isolating nucleic acids from the isolated immune cells, where the isolated nucleic acids encode for genes or proteins corresponding to the CDR3 region of the isolated immune cells, wherein the CDR3 region of the isolated immune cells encompasses 22 V-beta families;
amplifying the CDR3 region of the nucleic acid;
separating the amplified CDR3 fragments by length;
determining a prevalence of the amplified CDR3 fragments to provide an intrafamily gene fragment length profile for the CDR3 region; and
comparing the assay profile to a control intrafamily gene fragment length profile derived from blood cells of a healthy individual, to determine a presence or an absence of at least one gene fragment length that is more prevalent in the assay profile than the control profile, wherein the control profile is for the same TCR-CDR3 gene family as the assay profile;
wherein the presence of the more prevalent at least one gene fragment length CDR is indicative of the neurodegenerative disease; and
wherein the neurodegenerative disease is Parkinson's disease, or Alzheimer's disease.

14. The method of claim 13, wherein the nucleic acid is mRNA or DNA.

15. The method of claim 14, further comprising: performing polymerase chain reaction to generate complementary DNA from the mRNA.

16. The method of claim 13, wherein the immune cells are selectively isolated using $CD4^+$, $CD8^+$, $CD5^+$, or $CD27^+$.

17. The method of claim 16, wherein the immune cells are isolated using magnetic cell sorting.

18. The method of claim 16, wherein the immune cells are selectively isolated using $CD8^+$.

19. The method of claim 13, wherein the cells are derived from peripheral blood from the individual.

20. The method of claim 13, wherein the control profile is an averaged profile derived from a plurality of single TCR-CDR3 intrafamily gene fragment length profiles, and wherein each of said single profiles is derived from blood cells of a healthy, age-matched human subject.

* * * * *

SEQUENCE LISTING

<160> NUMBER OF SEQ ID NOS: 55

<210> SEQ ID NO 1
<211> LENGTH: 3
<212> TYPE: PRT
<213> ORGANISM: Homo sapiens

<400> SEQUENCE: 1

Cys Ala Thr
1

<210> SEQ ID NO 2
<211> LENGTH: 3
<212> TYPE: PRT
<213> ORGANISM: Homo sapiens

<400> SEQUENCE: 2

Cys Ala Thr
1

<210> SEQ ID NO 3
<211> LENGTH: 3
<212> TYPE: PRT
<213> ORGANISM: Homo sapiens

<400> SEQUENCE: 3

Cys Ala Thr
1

<210> SEQ ID NO 4
<211> LENGTH: 3
<212> TYPE: PRT
<213> ORGANISM: Homo sapiens

<400> SEQUENCE: 4

Cys Ala Thr
1

<210> SEQ ID NO 5
<211> LENGTH: 3
<212> TYPE: PRT
<213> ORGANISM: Homo sapiens

<400> SEQUENCE: 5

Cys Ala Thr
1

<210> SEQ ID NO 6
<211> LENGTH: 3
<212> TYPE: PRT
<213> ORGANISM: Homo sapiens

<400> SEQUENCE: 6

Cys Ala Thr
1

<210> SEQ ID NO 7
<211> LENGTH: 3
<212> TYPE: PRT
<213> ORGANISM: Homo sapiens

<400> SEQUENCE: 7

Cys Ala Thr
1

```
<210> SEQ ID NO 8
<211> LENGTH: 3
<212> TYPE: PRT
<213> ORGANISM: Homo sapiens

<400> SEQUENCE: 8

Cys Ala Thr
1

<210> SEQ ID NO 9
<211> LENGTH: 3
<212> TYPE: PRT
<213> ORGANISM: Homo sapiens

<400> SEQUENCE: 9

Cys Ala Ser
1

<210> SEQ ID NO 10
<211> LENGTH: 3
<212> TYPE: PRT
<213> ORGANISM: Homo sapiens

<400> SEQUENCE: 10

Cys Ala Ser
1

<210> SEQ ID NO 11
<211> LENGTH: 3
<212> TYPE: PRT
<213> ORGANISM: Homo sapiens

<400> SEQUENCE: 11

Cys Ala Ser
1

<210> SEQ ID NO 12
<211> LENGTH: 3
<212> TYPE: PRT
<213> ORGANISM: Homo sapiens

<400> SEQUENCE: 12

Cys Ala Ser
1

<210> SEQ ID NO 13
<211> LENGTH: 3
<212> TYPE: PRT
<213> ORGANISM: Homo sapiens

<400> SEQUENCE: 13

Cys Ala Ser
1

<210> SEQ ID NO 14
<211> LENGTH: 3
<212> TYPE: PRT
<213> ORGANISM: Homo sapiens

<400> SEQUENCE: 14

Cys Ala Ser
1
```

```
<210> SEQ ID NO 15
<211> LENGTH: 3
<212> TYPE: PRT
<213> ORGANISM: Homo sapiens

<400> SEQUENCE: 15

Cys Ala Ser
1

<210> SEQ ID NO 16
<211> LENGTH: 3
<212> TYPE: PRT
<213> ORGANISM: Homo sapiens

<400> SEQUENCE: 16

Cys Ala Ser
1

<210> SEQ ID NO 17
<211> LENGTH: 3
<212> TYPE: PRT
<213> ORGANISM: Homo sapiens

<400> SEQUENCE: 17

Cys Ala Ser
1

<210> SEQ ID NO 18
<211> LENGTH: 10
<212> TYPE: PRT
<213> ORGANISM: Homo sapiens

<400> SEQUENCE: 18

Tyr Pro Gly Leu Ala Asp Asn Glu Gln Phe
1               5                   10

<210> SEQ ID NO 19
<211> LENGTH: 10
<212> TYPE: PRT
<213> ORGANISM: Homo sapiens

<400> SEQUENCE: 19

Tyr Pro Gly Leu Ala Asp Asn Glu Gln Phe
1               5                   10

<210> SEQ ID NO 20
<211> LENGTH: 10
<212> TYPE: PRT
<213> ORGANISM: Homo sapiens

<400> SEQUENCE: 20

Tyr Pro Gly Leu Ala Asp Asn Glu Gln Phe
1               5                   10

<210> SEQ ID NO 21
<211> LENGTH: 10
<212> TYPE: PRT
<213> ORGANISM: Homo sapiens

<400> SEQUENCE: 21

Tyr Pro Gly Leu Ala Asp Asn Glu Gln Phe
1               5                   10
```

```
<210> SEQ ID NO 22
<211> LENGTH: 10
<212> TYPE: PRT
<213> ORGANISM: Homo sapiens

<400> SEQUENCE: 22

Tyr Pro Gly Leu Ala Asp Asn Glu Gln Phe
1               5                   10

<210> SEQ ID NO 23
<211> LENGTH: 10
<212> TYPE: PRT
<213> ORGANISM: Homo sapiens

<400> SEQUENCE: 23

Tyr Pro Gly Leu Ala Asp Asn Glu Gln Phe
1               5                   10

<210> SEQ ID NO 24
<211> LENGTH: 10
<212> TYPE: PRT
<213> ORGANISM: Homo sapiens

<400> SEQUENCE: 24

Tyr Pro Gly Leu Ala Asp Asn Glu Gln Phe
1               5                   10

<210> SEQ ID NO 25
<211> LENGTH: 10
<212> TYPE: PRT
<213> ORGANISM: Homo sapiens

<400> SEQUENCE: 25

Tyr Pro Gly Leu Ala Asp Asn Glu Gln Phe
1               5                   10

<210> SEQ ID NO 26
<211> LENGTH: 10
<212> TYPE: PRT
<213> ORGANISM: Homo sapiens

<400> SEQUENCE: 26

Tyr Pro Gly Leu Ala Asp Asn Glu Gln Phe
1               5                   10

<210> SEQ ID NO 27
<211> LENGTH: 10
<212> TYPE: PRT
<213> ORGANISM: Homo sapiens

<400> SEQUENCE: 27

Tyr Pro Gly Leu Ala Asp Asn Glu Gln Phe
1               5                   10

<210> SEQ ID NO 28
<211> LENGTH: 8
<212> TYPE: PRT
<213> ORGANISM: Homo sapiens

<400> SEQUENCE: 28

Ser Pro Thr Gly Asn Glu Gln Phe
1               5
```

```
<210> SEQ ID NO 29
<211> LENGTH: 8
<212> TYPE: PRT
<213> ORGANISM: Homo sapiens

<400> SEQUENCE: 29

Ser Pro Thr Gly Asn Glu Gln Phe
1               5

<210> SEQ ID NO 30
<211> LENGTH: 8
<212> TYPE: PRT
<213> ORGANISM: Homo sapiens

<400> SEQUENCE: 30

Ser Pro Thr Gly Asn Glu Gln Phe
1               5

<210> SEQ ID NO 31
<211> LENGTH: 11
<212> TYPE: PRT
<213> ORGANISM: Homo sapiens

<400> SEQUENCE: 31

Ser Tyr Asn Phe Gly Ser Asn Glu Lys Leu Phe
1               5                   10

<210> SEQ ID NO 32
<211> LENGTH: 11
<212> TYPE: PRT
<213> ORGANISM: Homo sapiens

<400> SEQUENCE: 32

Ser Tyr Asn Phe Gly Ser Asn Glu Lys Leu Phe
1               5                   10

<210> SEQ ID NO 33
<211> LENGTH: 11
<212> TYPE: PRT
<213> ORGANISM: Homo sapiens

<400> SEQUENCE: 33

Ser Tyr Asn Phe Gly Ser Asn Glu Lys Leu Phe
1               5                   10

<210> SEQ ID NO 34
<211> LENGTH: 11
<212> TYPE: PRT
<213> ORGANISM: Homo sapiens

<400> SEQUENCE: 34

Ser Tyr Asn Phe Gly Ser Asn Glu Lys Leu Phe
1               5                   10

<210> SEQ ID NO 35
<211> LENGTH: 11
<212> TYPE: PRT
<213> ORGANISM: Homo sapiens

<400> SEQUENCE: 35

Ser Tyr Asn Phe Gly Ser Asn Glu Lys Leu Phe
1               5                   10
```

```
<210> SEQ ID NO 36
<211> LENGTH: 11
<212> TYPE: PRT
<213> ORGANISM: Homo sapiens

<400> SEQUENCE: 36

Ser Tyr Asn Phe Gly Ser Asn Glu Lys Leu Phe
1               5                   10

<210> SEQ ID NO 37
<211> LENGTH: 8
<212> TYPE: PRT
<213> ORGANISM: Homo sapiens

<400> SEQUENCE: 37

Phe Gly Pro Gly Thr Arg Leu Thr
1               5

<210> SEQ ID NO 38
<211> LENGTH: 8
<212> TYPE: PRT
<213> ORGANISM: Homo sapiens

<400> SEQUENCE: 38

Phe Gly Pro Gly Thr Arg Leu Thr
1               5

<210> SEQ ID NO 39
<211> LENGTH: 8
<212> TYPE: PRT
<213> ORGANISM: Homo sapiens

<400> SEQUENCE: 39

Phe Gly Pro Gly Thr Arg Leu Thr
1               5

<210> SEQ ID NO 40
<211> LENGTH: 8
<212> TYPE: PRT
<213> ORGANISM: Homo sapiens

<400> SEQUENCE: 40

Phe Gly Pro Gly Thr Arg Leu Thr
1               5

<210> SEQ ID NO 41
<211> LENGTH: 8
<212> TYPE: PRT
<213> ORGANISM: Homo sapiens

<400> SEQUENCE: 41

Phe Gly Pro Gly Thr Arg Leu Thr
1               5

<210> SEQ ID NO 42
<211> LENGTH: 8
<212> TYPE: PRT
<213> ORGANISM: Homo sapiens

<400> SEQUENCE: 42

Phe Gly Pro Gly Thr Arg Leu Thr
1               5
```

```
<210> SEQ ID NO 43
<211> LENGTH: 8
<212> TYPE: PRT
<213> ORGANISM: Homo sapiens

<400> SEQUENCE: 43

Phe Gly Pro Gly Thr Arg Leu Thr
1               5

<210> SEQ ID NO 44
<211> LENGTH: 8
<212> TYPE: PRT
<213> ORGANISM: Homo sapiens

<400> SEQUENCE: 44

Phe Gly Pro Gly Thr Arg Leu Thr
1               5

<210> SEQ ID NO 45
<211> LENGTH: 8
<212> TYPE: PRT
<213> ORGANISM: Homo sapiens

<400> SEQUENCE: 45

Phe Gly Pro Gly Thr Arg Leu Thr
1               5

<210> SEQ ID NO 46
<211> LENGTH: 8
<212> TYPE: PRT
<213> ORGANISM: Homo sapiens

<400> SEQUENCE: 46

Phe Gly Pro Gly Thr Arg Leu Thr
1               5

<210> SEQ ID NO 47
<211> LENGTH: 7
<212> TYPE: PRT
<213> ORGANISM: Homo sapiens

<400> SEQUENCE: 47

Phe Gly Pro Gly Thr Arg Leu
1               5

<210> SEQ ID NO 48
<211> LENGTH: 7
<212> TYPE: PRT
<213> ORGANISM: Homo sapiens

<400> SEQUENCE: 48

Phe Gly Pro Gly Thr Arg Leu
1               5

<210> SEQ ID NO 49
<211> LENGTH: 7
<212> TYPE: PRT
<213> ORGANISM: Homo sapiens

<400> SEQUENCE: 49

Phe Gly Pro Gly Thr Arg Leu
1               5
```

-continued

```
<210> SEQ ID NO 50
<211> LENGTH: 7
<212> TYPE: PRT
<213> ORGANISM: Homo sapiens

<400> SEQUENCE: 50

Phe Gly Ser Gly Thr Gln Leu
1               5

<210> SEQ ID NO 51
<211> LENGTH: 7
<212> TYPE: PRT
<213> ORGANISM: Homo sapiens

<400> SEQUENCE: 51

Phe Gly Ser Gly Thr Gln Leu
1               5

<210> SEQ ID NO 52
<211> LENGTH: 7
<212> TYPE: PRT
<213> ORGANISM: Homo sapiens

<400> SEQUENCE: 52

Phe Gly Ser Gly Thr Gln Leu
1               5

<210> SEQ ID NO 53
<211> LENGTH: 7
<212> TYPE: PRT
<213> ORGANISM: Homo sapiens

<400> SEQUENCE: 53

Phe Gly Ser Gly Thr Gln Leu
1               5

<210> SEQ ID NO 54
<211> LENGTH: 7
<212> TYPE: PRT
<213> ORGANISM: Homo sapiens

<400> SEQUENCE: 54

Phe Gly Ser Gly Thr Gln Leu
1               5

<210> SEQ ID NO 55
<211> LENGTH: 7
<212> TYPE: PRT
<213> ORGANISM: Homo sapiens

<400> SEQUENCE: 55

Phe Gly Ser Gly Thr Gln Leu
1               5
```